(12) United States Patent
Hazin et al.

(10) Patent No.: US 6,919,472 B2
(45) Date of Patent: Jul. 19, 2005

(54) CATALYST COMPOSITIONS FOR THE SELECTIVE CONVERSION OF ALKANES TO UNSATURATED CARBOXYLIC ACIDS, METHODS OF MAKING AND METHODS OF USING THEREOF

(75) Inventors: Paulette N. Hazin, Houston, TX (US); Paul E. Ellis, Jr., Sugar Land, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 10/325,093

(22) Filed: Dec. 20, 2002

(65) Prior Publication Data

US 2003/0135071 A1 Jul. 17, 2003

Related U.S. Application Data

(60) Provisional application No. 60/344,873, filed on Dec. 21, 2001.

(51) Int. Cl.$^7$ ............................................... B01J 29/06
(52) U.S. Cl. ..................... 558/321; 568/910; 568/959; 502/311; 502/312; 502/317; 502/321; 502/347; 502/353; 502/354; 502/348; 502/300; 502/324; 502/303; 502/304; 502/308; 502/310; 502/349; 502/352; 502/313; 502/316; 502/325; 502/338; 502/344; 502/319; 502/322; 502/323; 502/355; 502/208; 502/209; 502/211
(58) Field of Search ................................ 502/311, 312, 502/317, 321, 347, 353, 354, 348, 300, 324, 303, 304, 308, 310, 349, 352, 313, 316, 325, 338, 344, 319, 322, 323, 355, 208, 209, 211; 568/910, 959; 558/321

(56) References Cited

U.S. PATENT DOCUMENTS

| | | | |
|---|---|---|---|
| 4,250,346 A | | 2/1981 | Young et al. |
| 4,256,914 A | * | 3/1981 | Umemura et al. ........... 562/535 |
| 4,339,355 A | | 7/1982 | Decker et al. |
| 5,380,933 A | | 1/1995 | Ushikubo et al. |
| 5,807,531 A | | 9/1998 | Hibst et al. |
| 5,994,580 A | | 11/1999 | Takahashi et al. |
| 6,087,525 A | * | 7/2000 | Abdulwahed et al. ....... 558/321 |
| 6,160,162 A | | 12/2000 | Karim et al. |
| 6,432,870 B1 | * | 8/2002 | Tu et al. ..................... 502/305 |
| 6,656,873 B2 | * | 12/2003 | Chaturvedi et al. ......... 502/312 |
| 2003/0004379 A1 | * | 1/2003 | Gaffney et al. ............. 568/910 |

FOREIGN PATENT DOCUMENTS

| | | |
|---|---|---|
| CN | 1159960 | 9/1997 |
| DE | 19622331 A1 | 6/1996 |
| EP | 0962253 A2 | 12/1999 |
| JP | 6218286 | 8/1994 |
| JP | 10045664 | 2/1998 |
| JP | 10057813 | 3/1998 |
| JP | 10120617 | 5/1998 |
| JP | 10310539 | 11/1998 |
| JP | 11114418 | 4/1999 |
| JP | 2000246108 | 9/2000 |
| WO | WO 99/51339 | * 10/1999 |

* cited by examiner

Primary Examiner—Christina Johnson
(74) Attorney, Agent, or Firm—Jim Wheelington

(57) ABSTRACT

A catalyst composition for the selective conversion of an alkane to an unsaturated carboxylic acid having the general formula:

$$MoV_aNb_bAg_cM_dO_x$$

wherein optional element M may be one or more selected from aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum; a is 0.05 to 0.99, b is 0.01 to 0.99, c is 0.01 to 0.99, d is 0 to 0.5 and x is determined by the valence requirements of the other components of the catalyst composition. This catalyst is prepared by co-precipitation of compounds of molybdenum, vanadium, niobium, silver and M to form a mixed metal oxide catalyst. This catalyst can be used for the selective conversion of an alkane to an unsaturated carboxylic acid in a one-step process or the ammoxidation of alkanes and olefins.

75 Claims, No Drawings

CATALYST COMPOSITIONS FOR THE SELECTIVE CONVERSION OF ALKANES TO UNSATURATED CARBOXYLIC ACIDS, METHODS OF MAKING AND METHODS OF USING THEREOF

This application claims the benefit of Provisional Application No. 60/344,873, filed Dec. 21, 2001.

BACKGROUND OF THE INVENTION

1. Field of the Invention

This invention relates to a catalyst for producing an unsaturated carboxylic acid from an alkane, a method of making said catalyst and a method of using said catalyst. In particular, this invention relates to a catalyst for producing acrylic acid from propane by a single step vapor phase oxidation reaction.

2. Description of the Prior Art

The production of an unsaturated carboxylic acid, such as acrylic acid or methacrylic acid, is conventionally done by catalytically reacting an olefin, such as propylene or isobutylene, with oxygen to form an alkenylaldehyde, such as acrolein or methacrolein, which is subsequently catalytically reacted with oxygen. Alkanes, such as propane, have advantages of cost and of availability over olefins. Furthermore, a one step process would have advantages over the present commercial process.

There are instances of producing acrylic acid and other unsaturated carboxylic acids from propane and other alkanes in a one step vapor phase catalytic oxidation reaction. U.S. Pat. No. 5,380,933 discloses a catalyst of oxides of molybdenum, vanadium, tellurium, and elements selected from niobium, tantalum, tungsten, titanium, aluminum, zirconium, chromium, manganese, iron, ruthenium, cobalt, rhodium, nickel, palladium, platinum, antimony, bismuth, boron, indium or cerium. Japanese published patent application H10-57813 discloses a metal oxide catalyst of molybdenum, vanadium, tellurium and/or antimony and an element selected from niobium, tantalum, tungsten, titanium, aluminum, zirconium, chromium, manganese, iron, ruthenium, cobalt, rhodium, nickel, palladium, platinum, bismuth, boron, indium, phosphorus, rare earth elements, alkali metals, alkali-earth metals. Japanese published patent application H10-45664 discloses a catalyst of oxides of molybdenum, vanadium, antimony and an element selected from niobium, tantalum, tungsten, titanium, zirconium, chromium, iron, manganese, ruthenium, cobalt, rhodium, nickel, palladium, platinum, boron, indium, alkali metals, alkali-earth metals, and rare earth elements. European published patent application 0 962 253 discloses a catalyst having oxides of molybdenum, tungsten, iron, niobium, tantalum, zirconium, ruthenium and mixtures thereof; vanadium, cerium, chromium and mixtures, thereof; tellurium, bismuth, antimony, selenium, and mixtures thereof; and niobium, tantalum, tungsten, titanium, aluminum, zirconium, chromium, manganese, iron, ruthenium, cobalt, rhenium, nickel, palladium, platinum, antimony, bismuth, boron, indium, cerium and mixtures thereof. Japanese issued patent no. 96-120,617 discloses a supported catalyst having oxides of molybdenum, vanadium, antimony, one of niobium, tantalum, tin, tungsten, titanium, nickel, iron, chromium or cobalt, and at least one of sodium, potassium, rubidium, cesium, phosphorus and arsenic. Japanese patent no. 00-246,108 discloses a catalyst having oxides of molybdenum, vanadium, antimony, at least one of niobium and tantalum and at least one of silver, zinc, tin, lead, arsenic, copper, thallium and selenium. Japanese published patent application H6-128286 disclosed a heteropolyacid catalyst having oxides of phosphorus, molybdenum, vanadium, at least one of arsenic and antimony, and at least one of tin, lead, cerium, cobalt, iron, zirconium, thorium, tungsten, germanium, nickel, rhenium, bismuth, chromium, boron, magnesium, calcium, barium, strontium, selenium, tellurium, silver, aluminum, zinc, copper, titanium, potassium, rubidium, cesium and thallium. U.S. Pat. Nos. 6,160,162 and 6,114,278 disclose a calcined catalyst having molybdenum, vanadium, gallium, palladium, niobium and at least one of lanthanum, tellurium, germanium, zinc, silicon, indium and tungsten. U.S. Pat. No. 5,994,580 discloses oxides of molybdenum, vanadium, antimony and at least one of niobium, tantalum, tin, tungsten, titanium, nickel, iron, chromium and cobalt. Japanese patent no. 11114418 discloses a catalyst having oxides of niobium, molybdenum, antimony, at least one of phosphorus, arsenic, boron, silicon and germanium and at least one of potassium, cesium, rubidium, calcium, magnesium, tellurium, chromium, manganese, iron, cobalt, nickel, cooper silver, lead, bismuth, aluminum, gallium, indium, tin, zinc, lanthanum, cerium, yttrium, tungsten, tantalum, ruthenium, rhodium, palladium, platinum, iridium, osmium, rhenium and hafnium. Chinese patent application 1,159,960 discloses bismuth based catalysts with vanadium, niobium, or tantalum and chromium, molybdenum or tungsten, optionally with lithium, sodium, potassium, copper, silver or gold. U.S. Pat. No. 4,339,355 discloses a catalyst having molybdenum, vanadium and niobium with chromium, cooper, manganese or yttrium. German patent application no. 19622331 discloses a catalyst having molybdenum, bismuth and phosphorus with vanadium, niobium, tantalum, chromium, tungsten, gallium, cerium or lanthanum; lithium, sodium, potassium, rubidium, cesium, copper, silver, gold, palladium or platinum; tin lead, antimony, bismuth, tellurium, iron, cobalt or nickel; and silicon, aluminum, titanium or zirconium. U.S. Pat. No. 5,807,531 discloses a catalyst having molybdenum and vanadium with tungsten, niobium, titanium, zirconium, hafnium, tantalum, chromium, silicon or germanium. Japanese patent application no. 246,108 (2000) discloses a catalyst having molybdenum, vanadium and antimony with niobium or tantalum and silver, zinc, tin, lead, arsenic, copper, thallium or selenium. Catalyst with similar compositions have been used for processes other than those for producing acrylic acid and other unsaturated carboxylic acids from propane and other alkanes in a one step vapor phase catalytic oxidation reaction. U.S. Pat. No. 4,250,346 discloses a catalyst for catalytically oxydehydrogenating ethane to ethylene, said catalyst having molybdenum with chromium, manganese, niobium, tantalum, titanium, vanadium or tungsten or bismuth, cerium, cobalt, copper, iron, potassium, magnesium, nickel, phosphorus, lead, antimony, silicon, tin, thallium or uranium. Japanese patent application no. 98 310,539 discloses a catalyst to form propylene from propane, said catalyst having molybdenum, vanadium and niobium.

While silver has been disclosed as a component in some of the catalysts discussed above, it is not a required component for any of these catalysts and the advantages and benefits of a catalyst composition in a one step process for producing an unsaturated carboxylic acid, such as acrylic acid or methacrylic acid, from an alkanes, such as propane, have not been disclosed.

U.S. Pat. No. 5,380,933 noted above discloses a molybdovanadate catalyst for the oxidation of propane to acrylic acid with a yield of 52%. The catalyst contains molybdenum, vanadium, niobium and tellurium. Tellurium can become volatile at the temperatures used for the oxidation of propane to acrylic acid (350–425° C.). Catalyst life can be affected by the loss of tellurium. In addition, tellurium is an environmental hazard which must be contained or controlled with means which add to the overall process costs. The present catalyst does not contain tellurium.

Japanese patent application no. H6-218286 noted above discloses a silver-containing molybdovanadate catalyst (0.1 gram-mole of silver per 12 gram-moles of molybdenum) for conversion of propane to acrolein and acrylic acid. The catalyst also contained phosphorus, copper, barium, tellurium, iron, cerium and potassium. The overall yield for acrylic acid was less than 0.2%. The silver-containing catalyst was not shown to have any advantages over other claimed catalysts. Silver was only one of twenty-nine possible elements in the claimed catalyst.

SUMMARY OF THE INVENTION

This invention is a silver-containing catalyst for use in a one step process for producing an unsaturated carboxylic acid, such as acrylic acid or methacrylic acid, from an alkane, such as propane or isobutane, a method of making a silver-containing catalyst and a method of producing an unsaturated carboxylic acid, such as acrylic acid or methacrylic acid, from an alkane, such as propane or isobutane, with a silver-containing catalyst. The catalyst has a composition of $MoV_aNb_bAg_cM_dO_x$ wherein optional element M is at least one element from aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum; a is 0.05 to 0.99, preferably 0.1 to 0.5, most preferably 0.2; b is 0.01 to 0.99, preferably 0.05 to 0.2, most preferably 0.06 to 0.12; c is 0.01 to 0.99, preferably 0.05 to 0.5, most preferably 0.12 to 0.35; d is 0 to 0.5, preferably 0.01 to 0.25, most preferably 0.02 to 0.1; and x is determined by the valence requirements of the other components of the catalyst composition.

DESCRIPTION OF EMBODIMENTS OF THE INVENTION

This invention is generally a mixed metal oxide catalyst and, more specifically, a molybdovanadate catalyst. The catalyst of the present invention is a mixture of oxides of molybdenum, vanadium, niobium and silver. In addition, it may contain oxides of other metals, such as aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum.

The catalyst of the present invention has the composition described in the following formulae:

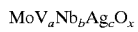

$MoV_aNb_bAg_cO_x$

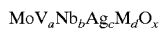

$MoV_aNb_bAg_cM_dO_x$ wherein optional element M may be one or more selected from aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum; a is 0.05 to 0.99, preferably 0.1 to 0.5, most preferably 0.2; b is 0.01 to 0.99, preferably 0.05 to 0.2, most preferably 0.06 to 0.12; c is 0.01 to 0.99, preferably 0.05 to 0.5, most preferably 0.12 to 0.35; d is 0 to 0.5, preferably 0.01 to 0.25, most preferably 0.02 to 0.1; and x is determined by the valence requirements of the other components of the catalyst composition.

This catalyst may be used in a one-step process for producing an unsaturated carboxylic acid, such as acrylic acid or methacrylic acid, from an alkane, such as propane or isobutane. The alkane is preferably one having three to eight carbon atoms and is most preferable propane or isobutane. The process is preferably a vapor phase reaction in which the catalyst in brought into contact with an alkane and oxygen. The molar ratio of alkane:oxygen is preferably in the range of from 0.05:1 to 10:1. The contact time for the reactants preferably is in the range of from 0.1 to 10 seconds, preferably 0.1 to 5 seconds. Steam may be added to the reaction gases. If steam is used, the molar ratio of alkane:steam is in the range from 0.05:1 to 10:1. In addition, an inert gas such as nitrogen, argon or helium may be used a carrier medium. If a carrier medium is used, the molar ratio of alkane:carrier preferably is in the range from 0.02:1 to 10:1.

The reaction temperature for the method of using the present invention is 320–450° C., preferably 350–400° C. The reaction pressure is 0 to 75 psig, preferably 5 to 50 psig.

The method of using the present invention will, in addition to the unsaturated carboxylic acid, produce byproducts, including an olefin. For example, when the alkane is propane, byproducts of carbon monoxide, carbon dioxide, acetic acid and propylene will be formed. The olefin, such as propylene, may be separated from the other byproducts and recycled into the feed stream. The catalyst and process of the present invention can convert an olefin into an unsaturated carboxylic acid, e.g., propylene into acrylic acid. In the alternative, the olefin may be separated from the other byproducts and converted to an unsaturated carboxylic acid in a separate process using known catalysts for converting an olefin into an unsaturated carboxylic acid or used in other processes to produce other products.

The catalyst of the present invention may be used as an unsupported catalyst or a supported catalyst. If supported, the support should be an inert solid which is chemically unreactive with any of the active components of the catalyst and is preferably silica, alumina, niobia, titania, zirconia or mixtures thereof. The catalyst may be affixed to the support by methods known in the art, including incipient wetness, slurried reactions and spray drying. The catalyst is not limited by shape, size or particle distribution and may be formed as appropriate for the reaction vessel in the process. Examples are powder, granules, spheres, cylinders, saddles, etc.

Preferably, the catalyst is prepared from a solution of water-soluble compounds of each of the component metals. If the compounds are insoluble in water, a slurry or suspension may be formed and thoroughly dispersed or mixed. In the alternative, a solvent other than water, such as an acid or an alkali, may be used. Heat may be applied to facilitate dissolution in the solvent. Generally, a mixture of compounds of the elements, such as salts of other complexes, in the approximate desired gram-atom ratio is dissolved to form a solution. The solution can be heated to help react the compounds. Hydrothermal techniques known in the art can be applied to use elevated temperatures and pressures in solution. The liquid solvent is removed and the resulting catalyst composition is dried and then calcined.

Suitable precursor molybdenum compounds are molybdenum salts, such as ammonium paramolybdate, molybdenum oxides, molybdic acids or molybdenum chlorides. Suitable precursor vanadium compounds are vanadium salts, such as ammonium metavanadate, vanadium oxides, vanadium oxalates or vanadium sulfates.

Suitable precursor niobium compounds are niobium oxalate, ammonium niobium oxalate, niobium oxide, hydrous niobium oxide or niobic acid. Oxalic acid and niobic acid may be dissolved in water to obtain a solution. With respect to the obtained solution, it is preferred that the molar ratio of oxalic acid to niobium is in the range of from 1:1 to 12:1, preferably from 3:1 to 6:1. A dicarboxylic acid other than oxalic acid, such as malonic acid, succinic acid, glutaric acid and adipic acid, or a tricarboxylic acid, such as citric acid, may be used with or without niobic acid to form a solution.

Suitable precursor silver compounds are silver oxide, silver acetate, silver carbonate, silver nitrate or silver halides, such as silver chloride. Suitable precursor compounds of other metals, such as aluminum, copper, lithium, sodium, potassium, rubidium, cesium, gallium, iron, rhenium, cobalt, chromium, manganese, indium, thallium, bismuth, germanium, tin, cerium or lanthanum, are salts such as oxalates, tartrates, citrates, nitrates, halides, carbonates, bicarbonates, hydroxides, oxides and the like with nitrate and oxalate salts being preferred when appropriate and available. For phosphorus and arsenic, appropriate precursor compounds would include ammonium hydrogen phosphate, ammonium phosphate, phosphorus pentoxide, phosphoric acid, phosphorus acid, arsenic acid and arsenic oxide.

The liquid solvent may be removed by filtration, evaporation or centrifuge. If heat is used during removal of the liquid, preferably the temperature will be in the range from 40 to 100° C. Drying the catalyst composition is by methods known in the art. Spray drying may be used as a means to remove the liquid solvent and dry the catalyst in a single operation. After the catalyst composition is dried, preferably it is heat treated in air at a temperature in the range of 250–350° C. for 1 to 10 hours. Calcination of the catalyst composition preferably occurs in an inert gas, such as argon or nitrogen, at a temperature in the range of 550–650° C. for 1 to 10 hours. The solid catalyst may be further prepared by high-energy ballmilling with a planetary ballmill or lower energy grinding or crushing means to obtain desired particle size, particle shape and/or particle size distribution.

There are two factors which contribute to a catalyst being useful for oxidation of an alkane to an unsaturated carboxylic acid. The first factor is the degree to which the alkane is converted (% conversion). The second is the extent to which the desired product is obtained (% selectivity). The product of these two factors in turn determine the overall yield of the catalyst in the oxidation of an alkane to an unsaturated carboxylic acid. The catalyst of the catalyst of the present invention can attain a conversion of propane of 43% and a selectivity to acrylic acid of 49% for an overall yield of 21%.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

A mixed metal oxide with a nominal composition of $MoV_{0.3}Nb_{0.12}Ag_{0.23}O_x$ was prepared as follows:

Solution A: in 400 mL of warm water 40.12 g ammonium paramolybdate were dissolved followed by 7.97 g of ammonium metavanadate. The solution was allowed to cool to ambient temperature.

Solution B: in 160 mL of water 20.62 g of oxalic acid dihydrate and 4.65 g of niobic acid were heated for ½ hour to form a solution. The solution was allowed to cool to ambient temperature.

Solution C: 8.88 g of silver nitrate was dissolved in 40 mL of water at ambient temperature.

Solution B was added to solution A with stirring followed by solution C to obtain a slurry. The slurry was stirred overnight. Water was evaporated from the slurry at 50° C. to form a paste. The paste was dried in the oven for several days to from a solid product.

The obtained solid was calcined in air for 5 hours at 300° C. then in a stream of argon at 600° C. The solid was then crushed, pressed and sieved and the fraction of 18 to 35 mesh was tested.

EXAMPLE 2

A mixed metal oxide with a nominal composition of $MoV_{0.2}Nb_{0.12}Ag_{0.23}O_x$ was prepared in a similar manner as in Example 1 except that the amount of ammonium metavanadate used was 5.32 g.

EXAMPLE 3

A mixed metal oxide with a nominal composition of $MoV_{0.3}Nb_{0.12}Ag_{0.18}O_x$ was prepared in a similar manner as in Example 1 except that the amount of silver nitrate used was 6.95 g.

EXAMPLE 4

A mixed metal oxide with a nominal composition of $MoV_{0.3}Nb_{0.06}Ag_{0.12}O_x$ was prepared in a similar manner as in Example 1 except that the amounts of niobic acid, oxalic acid and silver nitrate used were 2.33 g, 13.75 g, and 4.63 g respectively.

EXAMPLE 5

A mixed metal oxide with a nominal composition of $MoV_{0.3}Nb_{0.06}Ag_{0.35}O_x$ was prepared in a similar manner as in Example 4 except that the amounts of silver nitrate used was 13.51 g.

EXAMPLE 6

A mixed metal oxide with a nominal composition of $MoV_{0.3}Nb_{0.12}Ag_{0.23}Cs_{0.02}O_x$ was prepared in a similar manner as in Example 1 except that 0.88 g of cesium nitrate was added to solution C.

EXAMPLE 7

A mixed metal oxide with a nominal composition of $MoV_{0.3}Nb_{0.12}Ag_{0.23}Al_{0.10}O_x$ was prepared in a similar manner as in Example 1 except that 8.52 g of aluminum nitrate was added to solution C.

EXAMPLE 8

A mixed metal oxide with a nominal composition of $MoV_{0.3}Nb_{0.12}Ag_{0.23}Ga_{0.03}O_x$ was prepared in a similar manner as in Example 1 except that 0.639 g of gallium oxide in 20 mL of water was added to the reaction mixture after the addition of solution C.

EXAMPLE 9

A mixed metal oxide with a nominal composition of $MoV_{0.3}Nb_{0.12}Ag_{0.12}P_{0.05}O_x$ was prepared in a similar manner as in Example 1 except that 1.31 g of phosphoric acid in 40 mL of water was added to the silver nitrate to form solution C.

COMPARATIVE EXAMPLE 10

A mixed metal oxide with a nominal composition of $MoV_{0.3}Nb_{0.12}O_x$ was prepared as follows:

Solution A: in 655 mL of warm water 40.12 g ammonium paramolybdate were dissolved followed by 7.93 g of ammonium metavanadate. The solution was allowed to cool to ambient temperature.

Solution B: in 160 mL of water 17.0 g of niobium oxalate were suspended at ambient temperature.

Solution B was added to solution A with stirring to obtain a yellow solution. Water was evaporated from the solution at 50° C. to form a paste. The paste was dried in the oven for several days to from a solid product.

The obtained solid was calcined in a stream of argon at 600° C. The solid was then crushed, pressed and sieved and the fraction of 18 to 35 mesh was tested.

COMPARATIVE EXAMPLE 11

A mixed metal oxide with a nominal composition of $MoV_{0.3}Nb_{0.12}Zn_{0.23}O_x$ was prepared in a similar manner as in Example 1 except that 15.55 g of zinc nitrate were used in place of silver nitrate.

COMPARATIVE EXAMPLE 12

A mixed metal oxide with a nominal composition of $MoV_{0.3}Nb_{0.12}Ni_{0.23}O_x$ was prepared in a similar manner as in Example 1 except that 15.20 g of nickel(II) nitrate were used in place of silver nitrate.

COMPARATIVE EXAMPLE 13

A mixed metal oxide with a nominal composition of $MoV_{0.3}Nb_{0.12}Al_{0.23}O_x$ was prepared in a similar manner as in Example 1 except that 19.60 g of aluminum nitrate were used in place of silver nitrate.

COMPARATIVE EXAMPLE 14

A mixed metal oxide with a nominal composition of $MoV_{0.3}Nb_{0.12}Cu_{0.23}O_x$ was prepared in a similar manner as in Example 1 except that 12.63 g of copper nitrate were used in place of silver nitrate.

For each of the catalysts from the Examples above, 2.5 cc of catalyst mixed with 2.5 cc of quartz chips were placed into a downflow packed bed reactor. The reactor was heated to a temperature as specified in Tables and 2. A mixture of propane, oxygen, nitrogen and steam was supplied to the reactor at a percent by volume and a rate as specified in Tables 1 and 2. The reaction continued at the pressure specified in Tables 1 and 2 and for at least three hours. The % conversion and the %selectivity were calculated and are reported in Tables 1 and 2.

TABLE 1

| Run # | Catalyst Example | Catalyst Composition | Feed Composition Propane/$O_2$/$N_2$/$H_2O$ | SV ($h^{-1}$) | Pressure Psig | Temp. ° C. | % Conversion | % Selectivity | % Yield |
|---|---|---|---|---|---|---|---|---|---|
| 1 | 1 | $MoV_{0.3}Nb_{0.12}Ag_{0.23}O_x$ | 2.2/6.7/60.0/31.1 | 3200 | 20 | 380 | 49.4 | 26.7 | 13.2 |
| 2 | 1 | " | 2.2/6.7/60.0/31.1 | 3200 | 20 | 360 | 37.5 | 38.3 | 14.4 |
| 3 | 1 | " | 2.2/6.7/60.0/31.1 | 3200 | 20 | 350 | 32.0 | 44.3 | 14.2 |
| 4 | 1 | " | 2.2/6.7/60.0/31.1 | 3200 | 10 | 380 | 41.5 | 32.0 | 13.3 |
| 5 | 1 | " | 3.1/5.0/45.0/46.9 | 3300 | 20 | 370 | 30.2 | 33.3 | 10.1 |
| 6 | 1 | " | 3.1/5.0/45.0/46.9 | 3300 | 20 | 360 | 25.1 | 39.7 | 10.0 |
| 7 | 1 | " | 2.2/6.7/60.0/31.1 | 3200 | 32 | 360 | 37.1 | 41.6 | 15.4 |
| 8 | 1 | " | 11.8/5.9/52.9/29.4 | 3900 | 20 | 350 | 14.0 | 45.7 | 6.4 |
| 9 | 1 | " | 6.2/6.2/56.2/31.3 | 3700 | 20 | 350 | 16.0 | 45.4 | 7.3 |
| 10 | 2 | $MoV_{0.2}Nb_{0.12}Ag_{0.23}O_x$ | 2.2/6.7/60.0/31.1 | 3200 | 32 | 380 | 43.1 | 49.5 | 21.3 |
| 11 | 2 | $MoV_{0.2}Nb_{0.12}Ag_{0.23}O_x$ | 11.8/5.9/52.9/29.4 | 3900 | 20 | 360 | 11.9 | 54.1 | 6.4 |
| 12 | 3 | $MoV_{0.3}Nb_{0.12}Ag_{0.18}O_x$ | 2.2/6.7/60.0/31.1 | 2500 | 20 | 360 | 54.1 | 20.6 | 11.1 |
| 13 | 4 | $MoV_{0.3}Nb_{0.06}Ag_{0.12}O_x$ | 2.2/6.7/60.0/31.1 | 3200 | 32 | 360 | 50.4 | 29.6 | 14.9 |
| 14 | 5 | $MoV_{0.3}Nb_{0.06}Ag_{0.35}O_x$ | 2.2/6.7/60.0/31.1 | 3200 | 20 | 400 | 4.0 | 25.1 | 1.0 |
| 15 | 6 | $MoV_{0.3}Nb_{0.12}Ag_{0.23}Cs_{0.02}O_x$ | 2.2/6.7/60.0/31.1 | 2500 | 20 | 400 | 25.8 | 23.9 | 6.2 |
| 16 | 7 | $MoV_{0.3}Nb_{0.12}Ag_{0.23}Al_{0.10}O_x$ | 2.2/6.7/60.0/31.1 | 2500 | 20 | 400 | 21.4 | 20.8 | 4.5 |
| 17 | 8 | $MoV_{0.3}Nb_{0.12}Ag_{0.23}Ga_{0.03}O_x$ | 2.2/6.7/60.0/31.1 | 3300 | 20 | 380 | 50.0 | 21.7 | 10.8 |
| 18 | 9 | $MoV_{0.3}Nb_{0.12}Ag_{0.23}P_{0.05}O_x$ | 2.2/6.7/60.0/31.1 | 3200 | 32 | 370 | 45.4 | 36.1 | 16.4 |

TABLE 2

| Run # | Comparative Example | Catalyst Composition | Feed Composition Propane/$O_2$/ $N_2$/$H_2O$ | SV ($h^{-1}$) | Pressure Psig | Temp. °C. | % Conversion | % Selectivity | % Yield |
|---|---|---|---|---|---|---|---|---|---|
| 19 | 10 | $MoV_{0.3}Nb_{0.12}O_x$ | 2.2/6.7/ 60.0/31.1 | 1600 | 20 | 380 | 64.0 | 0.0 | 0.0 |
| 20 | 11 | $MoV_{0.3}Nb_{0.12}Zn_{0.23}O_x$ | 2.2/6.7/ 60.0/31.1 | 3200 | 20 | 380 | 26.9 | 1.9 | 0.5 |
| 21 | 12 | $MoV_{0.3}Nb_{0.12}Ni_{0.23}O_x$ | 2.2/6.7/ 60.0/31.1 | 3200 | 20 | 400 | 51.0 | 1.4 | 0.7 |
| 22 | 13 | $MoV_{0.3}Nb_{0.12}Al_{0.23}O_x$ | 2.2/6.7/ 60.0/31.1 | 3200 | 20 | 400 | 30.7 | 0.9 | 0.3 |
| 23 | 14 | $MoV_{0.3}Nb_{0.12}Cu_{0.23}O_x$ | 2.2/6.7/ 60.0/31.1 | 3200 | 20 | 380 | 7.9 | 3.3 | 0.3 |

The catalyst compositions of the above Examples for the production of acrylic acid have the general formula:

$$MoV_aNb_bAg_cM_dO_x$$

wherein Mo is molybdenum, V is vanadium, Nb is niobium, Ag is silver, optional element M may be one or more selected from aluminum, cesium, gallium or phosphorus; a is 0.02 to 0.3; b is 0.06 to 0.12; c is 0.12 to 0.35; d is 0 to 0.1; and x is determined by the valence requirements of the other components of the catalyst composition. These catalyst compositions can be made and used according to the processes disclose herein.

The X-ray diffraction pattern of the mixed metal oxide catalysts of the present invention is descriptive of the crystalline components of this catalyst. The catalyst compositions of the Examples above have a characteristic X-ray diffraction having four main diffraction peaks at the diffraction angles of 2θ, measured by using Cu Kα radiation:

TABLE 3

| Diffraction Angle 2θ (±0.3°) | d spacing (Å) | Relative Intensity |
|---|---|---|
| 22.3 | 3.99 | 100 |
| 26.2 | 3.40 | 30–80 |
| 27.0 | 3.30 | 30–80 |
| 27.7 | 3.21 | 20–80 |

There may be several additional diffraction peaks present in a catalyst composition of the present invention but these four peaks will normally be evident.

The Examples above demonstrate the benefits of the presence of silver in a mixed metal oxide molybdovanadate catalyst in the conversion of an alkane to an unsaturated carboxylic acid in a one-step process. Comparative Example 10 used a catalyst having oxides of molybdenum, vanadium and niobium only and, while the conversion of propane was higher for this catalyst than for any of the catalysts of Examples 1–5 which in addition to molybdenum, vanadium and niobium also contained silver, the selectivity to acrylic acid for the catalyst of Comparative Example 10 was nonexistent so that the overall yields for the silver-containing catalysts were favorable (0% v. 1.0–21.3%). The same advantage is seen when the catalyst of Comparative Example 13 having oxides of molybdenum, vanadium, niobium and aluminum only is compared to the catalyst of Example 7 in which silver is present in addition to molybdenum, vanadium, niobium and aluminum (0.3% v. 4.5% yield).

As can be seen from the above data, a feed composition having a high propane content (propane:oxygen molar ratios of approximately 2:1 and 1:1, Runs #8, #9 and #11, Table 1) with the catalyst of the present invention gives a reaction product with a high selectivity to acrylic acid (45.7%, 45.4% and 54.1%, respectively). Due to the excess propane in relation to oxygen, the % conversion is lower than for other runs having lower propane content (propane:oxygen molar ratios of approximately 0.33:1 and 0.6:1, Runs #1–7 and #10, Table 1). However, in a continuous process the unconverted propane could be recycled. A feed composition having a high propane content has the advantage of low flammability and decreases the possibility of explosion.

Obviously, numerous modifications and variations of the present invention are possible in light of the above teachings. It is therefore to be understood that within the scope of the appended claims, the invention may be practiced otherwise than as specifically described herein.

The catalyst of the present invention can be rejuvenated by adding the same compounds which may be used in the synthesis of the catalyst, e.g., molybdenum salts, such as ammonium paramolybdate, molybdenum oxides, molybdic acids or molybdenum chlorides; vanadium salts, such as ammonium metavanadate, vanadium oxides or vanadium sulfates; niobium oxalate, ammonium niobium oxalate, niobium oxide hydrous niobium oxide or niobic acid; silver oxide, silver acetate, silver carbonate, silver nitrate or silver halides, such as silver chloride; oxalates, tartrates, citrates, nitrates, halides, carbonates, bicarbonates, hydroxides, oxides of metals, such as aluminum, copper, lithium, sodium, potassium, rubidium, cesium, gallium, iron, rhenium, cobalt, chromium, manganese, indium, thallium, bismuth, germanium, tin, cerium or lanthanum; ammonium hydrogen phosphate, ammonium phosphate, phosphorus pentoxide, phosphoric acid, phosphorus acid, arsenic acid and arsenic oxide. If water-soluble, the desired compound can be added with water into the vessel containing the catalyst.

The catalyst and process of the present invention are applicable to different reaction systems, such as fixed bed, moving bed and fluidized bed reactors. The catalyst particle size and process conditions can be altered for the desired reaction system.

The catalyst of the present invention should be applicable to different processes, such as ammoxidation of alkanes and olefins, e.g., producing acrylonitrile from propane, oxygen and ammonia or producing methacrylonitrile from isobutane, oxygen and ammonia.

What is claimed is:

1. A catalyst composition for production of an unsaturated carboxylic acid from an alkane comprising a compound of the formula:

$$MoV_aNb_bAg_cO_x$$

wherein Mo is molybdenum, V is vanadium, Nb is niobium, Ag is silver, a is from 0.05 to 0.99, b is 0.01 to 0.99, c is 0.12 to 0.35, and x is determined by the valence requirements of the other elements present.

2. The catalyst composition of claim 1 wherein the formula is:

$$MoV_aNb_bAg_cM_dO_x$$

wherein M is one or more elements selected from the group consisting of aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum and d is 0 to 0.5.

3. The catalyst composition of claim 2 wherein M is cesium, aluminum, phosphorus or gallium and d is 0.02 to 0.1.

4. The catalyst composition of claim 2 wherein a is 0.1 to 0.5.

5. The catalyst composition of claim 4 wherein a is 0.2.

6. The catalyst composition of claim 2 wherein b is 0.05 to 0.2.

7. The catalyst composition of claim 6 wherein b is 0.06 to 0.12.

8. The catalyst composition of claim 2 wherein d is 0.01 to 0.25.

9. The catalyst composition of claim 8 wherein d is 0.02 to 0.1.

10. The catalyst composition of claim 1 selected from the group consisting of $MoV_{0.3}Nb_{0.6}Ag_{0.12}O_x$, $MoV_{0.3}Nb_{0.12}Ag_{0.18}O_x$, $MoV_{0.3}Nb_{0.12}Ag_{0.23}O_x$, $MoV_{0.2}Nb_{0.12}Ag_{0.23}O_x$, $MoV_{0.3}Nb_{0.06}Ag_{0.35}O_x$, $MoV_{0.3}Nb_{0.12}Ag_{0.23}Cs_{0.02}O_x$, $MoV_{0.3}Nb_{0.12}Ag_{0.23}Al_{0.10}O_x$, $MoV_{0.3}Nb_{0.12}Ag_{0.23}Ga_{0.03}O_x$ and $MoV_{0.3}Nb_{0.12}Ag_{0.23}P_{0.05}O_x$.

11. The catalyst composition of claim 1 having an X-ray diffraction pattern of four main diffraction peaks at the diffraction angles of 2θ, measured by using Cu Kα radiation, at 22.3, 26.2, 27.0 and 27.7.

12. The catalyst composition of claim 2 having an X-ray diffraction pattern of four main diffraction peaks at the diffraction angles of 2θ, measured by using Cu Kα radiation, at 22.3, 26.2, 27.0 and 27.7.

13. The catalyst composition of claim 2 wherein the catalyst composition is supported on an inert support.

14. The catalyst composition of claim 13 wherein the inert support is silica, alumina, niobia, titania, zirconia and mixtures thereof.

15. The catalyst composition of claim 2 wherein the catalyst composition is formed into powder, granules, spheres, cylinders or saddles.

16. A process of making a catalyst composition for production of an unsaturated carboxylic acid from an alkane comprising:
   a) forming a solution of a molybdenum compound, a vanadium compound, a niobium compound and a silver compound;
   b) mixing the solution to form a uniform solution;
   c) removing liquid from the uniform solution to form a solid;
   d) drying the solid;
   e) calcining the solid to form a catalyst of the formula:

$$MoV_aNb_bAg_cO_x$$

wherein Mo is molybdenum, V is vanadium, Nb is niobium, Ag is silver, a is 0.05 to 0.99, b is 0.01 to 0.99, c is 0.12 to 0.35, and x is determined by the valence requirements of the other elements present.

17. The process of claim 16 wherein the solution additionally comprises one of more compounds of M wherein M is an element selected from the group consisting of aluminum, copper, lithium, sodium, potassium, rubidium, cesium, gallium, phosphorus, iron, rhenium, cobalt, chromium, manganese, arsenic, indium, thallium, bismuth, germanium, tin, cerium and lanthanum to form a catalyst of the formula:

$$MoV_aNb_bAg_cM_dO_x$$

wherein d is 0 to 0.5.

18. The process of claim 17 wherein a is 0.1 to 0.5.

19. The process of claim 18 wherein a is 0.2.

20. The process of claim 17 wherein b is 0.05 to 0.2.

21. The process of claim 20 wherein b is 0.06 to 0.12.

22. The process of claim 17 wherein d is 0.01 to 0.25.

23. The process of claim 22 wherein d is 0.02 to 0.1.

24. The process of claim 17 wherein the molybdenum compound is ammonium paramolybdate, molybdenum oxide, molybdic acid or molybdenum chloride.

25. The process of claim 17 wherein the vanadium compound is ammonium metavanadate, vanadium oxide, vanadium oxalate or vanadium sulfate.

26. The process of claim 17 wherein the niobium compound is niobium oxalate, ammonium niobium oxalate, niobic acid, hydrous niobium oxide or niobium oxide.

27. The process of claim 17 wherein the niobium compound is formed from a solution of a dicarboxylic acid or a tricarboxylic acid and niobic acid dissolved in water.

28. The process of claim 27 wherein the dicarboxylic acid is oxalic acid.

29. The process of claim 28 wherein the molar ratio of oxalic acid to niobium is in the range of from 1:1 to 12:1.

30. The process of claim 29 wherein the molar ratio of oxalic acid to niobium is in the range from 3:1 to 6:1.

31. The process of claim 27 wherein the dicarboxylic acid is malonic acid, succinic acid, glutaric acid or adipic acid.

32. The process of claim 27 wherein the tricarboxylic acid is citric acid.

33. The process of claim 17 wherein the silver compound is silver oxide, silver acetate, silver carbonate, silver nitrate or silver chloride.

34. The process of claim 17 wherein the compound of M is an oxalate, tartrate, citrate, nitrate, halide, carbonate, bicarbonate, hydroxide or oxide of aluminum, copper, lithium, sodium, potassium, rubidium, cesium, gallium, iron, rhenium, cobalt, chromium, manganese, indium, thallium, bismuth, germanium, tin, cerium or lanthanum or is ammonium hydrogen phosphate, ammonium phosphate, phosphorus pentoxide, phosphoric acid, phosphorus acid, arsenic acid or arsenic oxide.

35. The process of claim 34 wherein the compound of M is a nitrate or oxalate.

36. The process of claim 34 wherein the compound of M is one of cesium nitrate, aluminum nitrate or gallium oxide.

37. The process of claim 17 additionally comprising supporting the catalyst on an inert support.

38. The process of claim 37 wherein the inert support is silica, alumina, niobia, titania, zirconia and mixtures thereof.

39. The process of claim 17 wherein the liquid solvent is removed by filtration, evaporation or centrifuge.

40. The process of claim 39 wherein the liquid solvent is removed by evaporation.

41. The process of claim 17 wherein the liquid is removed and the solid is dried by spray drying.

42. The process of claim 17 wherein after drying and before calcining the solid is heat treated in air at a temperature in the range of 250–350° C. for 1 to 10 hours.

43. The process of claim 17 wherein calcining occurs in an inert gas.

44. The process of claim 43 wherein the inert gas is argon or nitrogen.

45. The process of claim 17 wherein calcining is at a temperature in the range of 550–650° C. for 1 to 10 hours.

46. The process of claim 17 additionally comprising ballmilling, grinding or crushing the catalyst after calcining.

47. The process of claim 17 wherein the catalyst is selected from the group consisting of $MoV_{0.3}Nb_{0.06}Ag_{0.12}O_x$, $MoV_{0.3}Nb_{0.12}Ag_{0.18}O_x$, $MoV_{0.3}Nb_{0.12}Ag_{0.23}O_x$, $MoV_{0.2}Nb_{0.12}Ag_{0.23}O_x$, $MoV_{0.3}Nb_{0.06}Ag_{0.35}O_x$, $MoV_{0.3}Nb_{0.12}Ag_{0.23}Cs_{0.02}O_x$, $MoV_{0.3}Nb_{0.12}Ag_{0.23}Al_{0.10}O_x$, $MoV_{0.3}Nb_{0.12}Ag_{0.23}Ga_{0.03}O_x$ and $MoV_{0.3}Nb_{0.12}Ag_{0.23}P_{0.05}O_x$.

48. The process of claim 16 wherein the catalyst has an X-ray diffraction pattern of four main diffraction peaks at the diffraction angles of 2θ, measured by using Cu Kα radiation, at 22.3, 26.2, 27.0 and 27.7.

49. The process of claim 17 wherein the catalyst has an X-ray diffraction pattern of four main diffraction peaks at the diffraction angles of 2θ, measured by using Cu Kα radiation, at 22.3, 26.2, 27.0 and 27.7.

50. A process for producing an unsaturated carboxylic acid from an alkane comprising:

contacting an alkane and molecular oxygen with a catalyst composition of the formula:

$$MoV_aNb_bAg_cO_x$$

wherein Mo is molybdenum, V is vanadium, Nb is niobium, Ag is silver, a is 0.05 to 0.99, b is 0.01 to 0.99, c is 0/12 to 0.35 and x is determined by the valence requirements of the other elements present.

51. The process of claim 50 wherein the catalyst composition is of the formula:

$$MoV_aNb_bAg_cM_dO_x$$

wherein M is at least one elements selected from the group consisting of aluminum, copper, lithium, sodium, potassium, rubidium, cesium, gallium, phosphorus, iron, rhenium, cobalt, chromium, manganese, arsenic, indium, thallium, bismuth, germanium, tin, cerium and lanthanum and d is 0 to 0.5.

52. The process of claim 51 wherein M is cesium, aluminum or gallium and d is 0.02 to 0.1.

53. The process of claim 51 wherein a is 0.05 to 0.5.

54. The process of claim 53 wherein a is 0.2.

55. The process of claim 51 wherein b is 0.05 to 0.2.

56. The process of claim 55 wherein b is 0.06 to 0.12.

57. The process of claim 51 wherein d is 0.01 to 0.25.

58. The process of claim 57 wherein d is 0.02 to 0.1.

59. The process of claim 51 wherein the catalyst is a supported catalyst on an inert support.

60. The process of claim 59 wherein the inert support is silica, alumina, niobia, titania, zirconia or mixtures thereof.

61. The process of claim 51 wherein the catalyst composition is in the form of powder, granules, spheres, cylinders or saddles.

62. The process of claim 51 wherein the catalyst is selected from the group consisting of $MoV_{0.3}Nb_{0.06}Ag_{0.12}O_x$, $MoV_{0.3}Nb_{0.12}Ag_{0.18}O_x$, $MoV_{0.3}Nb_{0.12}Ag_{0.23}O_x$, $MoV_{0.2}Nb_{0.12}Ag_{0.23}O_x$, $MoV_{0.3}Nb_{0.06}Ag_{0.35}O_x$, $MoV_{0.3}Nb_{0.12}Ag_{0.23}Cs_{0.02}O_x$, $MoV_{0.3}Nb_{0.12}Ag_{0.23}Al_{0.10}O_x$, $MoV_{0.3}Nb_{0.12}Ag_{0.23}Ga_{0.03}O_x$ and $MoV_{0.3}Nb_{0.12}Ag_{0.23}P_{0.05}O_x$.

63. The process of claim 50 wherein the catalyst has an X-ray diffraction pattern of four main diffraction peaks at the diffraction angles of 2θ, measured by using Cu Kα radiation, at 22.3, 26.2, 27.0 and 27.7.

64. The process of claim 51 wherein the catalyst has an X-ray diffraction pattern of four main diffraction peaks at the diffraction angles of 2θ, measured by using Cu Kα radiation, at 22.3, 26.2, 27.0 and 27.7.

65. A catalyst composition for production of acrylic acid from propane comprising a compound of the formula:

$$MoV_aNb_bAg_cM_dO_x$$

wherein Mo is molybdenum, V is vanadium, Nb is niobium, Ag is silver, M is one or more elements selected from the group consisting of aluminum, copper, phosphorus, cesium and gallium, a is from 0.2 to 0.3, b is 0.06 to 0.12, c is 0.12 to 0.35 and d is 0 to 0.1 and x is determined by the valence requirements of the other elements present.

66. The catalyst composition of claim 65 wherein the catalyst has an X-ray diffraction pattern of four main diffraction peaks at the diffraction angles of 2θ, measured by using Cu Kα radiation, at 22.3, 26.2, 27.0 and 27.7.

67. The catalyst composition of claim 65 selected from the group consisting of $MoV_{0.3}Nb_{0.06}Ag_{0.12}O_x$, $MoV_{0.3}Nb_{0.12}Ag_{0.18}O_x$, $MoV_{0.3}Nb_{0.12}Ag_{0.23}O_x$, $MoV_{0.2}Nb_{0.12}Ag_{0.23}O_x$, $MoV_{0.3}Nb_{0.06}Ag_{0.35}O_x$, $MoV_{0.3}Nb_{0.12}Ag_{0.23}Cs_{0.02}O_x$, $MoV_{0.3}Nb_{0.12}Ag_{0.23}Al_{0.10}O_x$, $MoV_{0.3}Nb_{0.12}Ag_{0.23}Ga_{0.03}O_x$ and $MoV_{0.3}Nb_{0.12}Ag_{0.23}P_{0.05}O_x$.

68. A process of making a catalyst composition for production of acrylic acid from propane comprising:

a) forming a solution of a molybdenum compound, a vanadium compound, a niobium compound, a silver compound and a compound of M wherein M is selected from the group consisting of aluminum, copper, potassium, cesium and gallium;

b) mixing the solution to form a uniform solution;

c) removing liquid from the uniform solution to form a solid;

d) drying the solid;

e) calcining the solid to form a catalyst of the formula:

$$MoV_aNb_bAg_cM_dO_x$$

wherein Mo is molybdenum, V is vanadium, Nb is niobium, Ag is silver, M is aluminum, copper, potassium, cesium or gallium, a is from 0.2 to 0.3, b is 0.06 to 0.12, c is 0.12 to 0.35 and d is 0 to 0.23 and x is determined by the valence requirements of the other elements present.

69. The process of claim 68 wherein the catalyst composition has an X-ray diffraction pattern of four main diffraction peaks at the diffraction angles of 2θ, measured by using Cu Kα radiation, at 22.3, 26.2, 27.0 and 27.7.

70. The process of claim 68 wherein the catalyst composition is selected from the group consisting of $MoV_{0.3}Nb_{0.06}Ag_{0.12}O_x$, $MoV_{0.3}Nb_{0.12}Ag_{0.18}O_x$, $MoV_{0.3}Nb_{0.12}Ag_{0.23}O_x$, $MoV_{0.2}Nb_{0.12}Ag_{0.23}O_x$, $MoV_{0.3}Nb_{0.06}Ag_{0.35}O_x$, $MoV_{0.3}Nb_{0.12}Ag_{0.23}Cs_{0.02}O_x$, $MoV_{0.3}Nb_{0.12}Ag_{0.23}Al_{0.10}O_x$, $MoV_{0.3}Nb_{0.12}Ag_{0.23}Ga_{0.03}O_x$ and $MoV_{0.3}Nb_{0.12}Ag_{0.23}P_{0.05}O_x$.

71. A process for producing acrylic acid from propane comprising:

contacting propane and molecular oxygen with a catalyst composition of the formula:

$$MoV_aNb_bAg_cM_dO_x$$

wherein Mo is molybdenum, V is vanadium, Nb is niobium, Ag is silver, M is selected from the group consisting of aluminum, copper, potassium, cesium and gallium, a is from 0.2 to 0.3, b is 0.06 to 0.12, c is 0.12 to 0.35 and d is 0 to 0.1 and x is determined by the valence requirements of the other elements present.

72. The process of claim 71 wherein the catalyst composition has an X-ray diffraction pattern of four main diffraction peaks at the diffraction angles of 2θ, measured by using Cu Kα radiation, at 22.3, 26.2, 27.0 and 27.7.

73. The process of claim 71 wherein the catalyst is selected from the group consisting of $MoV_{0.3}Nb_{0.06}Ag_{0.12}O_x$, $MoV_{0.3}Nb_{0.12}Ag_{0.18}O_x$, $MoV_{0.3}Nb_{0.12}Ag_{0.23}O_x$, $MoV_{0.2}Nb_{0.12}Ag_{0.23}O_x$, $MoV_{0.3}Nb_{0.06}Ag_{0.35}O_x$, $MoV_{0.3}Nb_{0.12}Ag_{0.23}Cs_{0.02}O_x$, $MoV_{0.3}Nb_{0.12}Ag_{0.23}Al_{0.10}O_x$, $MoV_{0.3}Nb_{0.12}Ag_{0.23}Ga_{0.03}O_x$ and $MoV_{0.3}Nb_{0.12}Ag_{0.23}P_{0.05}O_x$.

74. The process of claim 71 in which the propane:oxygen molar ratio is in the range from 1:1 to 2:1.

75. A process for ammoxidation of alkanes to produce acrylonitrile or methacrylonitrile comprising:

contacting oxygen, ammonia and an alkane selected from the group consisting of propane and isobutane with a catalyst composition of the formula:

$$MoV_aNb_bAg_cM_dO_x$$

wherein Mo is molybdenum, V is vanadium, Nb is niobium, Ag is silver, M is selected from the group consisting of aluminum, copper, potassium, cesium and gallium, a is from 0.2 to 0.3, b is 0.06 to 0.12, c is 0.12 to 0.35 and d is 0 to 0.1 and x is determined by the valence requirements of the other elements present.

* * * * *